United States Patent [19]
Arduengo, III

[11] Patent Number: 5,162,482
[45] Date of Patent: Nov. 10, 1992

[54] 1,3-DIALKYLIMIDAZOLE-2-THIONE CATALYSTS AND METHOD OF MAKING SAME

[75] Inventor: Anthony J. Arduengo, III, Wilmington, Del.

[73] Assignee: E. I. Du Pont de Nemours and Company, Wilmington, Del.

[21] Appl. No.: 649,430

[22] Filed: Jan. 31, 1991

Related U.S. Application Data

[63] Continuation of Ser. No. 389,895, Aug. 4, 1989, abandoned.

[51] Int. Cl.$^5$ .................... C07G 233/30; C08G 59/68
[52] U.S. Cl. .................................. 528/94; 548/325.1; 548/324.1; 548/324.5; 548/323.5; 548/417
[58] Field of Search ................... 548/317, 310; 528/94

[56] References Cited

PUBLICATIONS

CA114:23205g Polarographic . . . Carbimazole, Zuman et al. 1990, p. 637.
CA 87:39372u S-Alkylation . . . Conditions: Hassanaly et al., 1977, p. 39367.

*Primary Examiner*—Mary C. Lee
*Assistant Examiner*—Joseph K. McKane
*Attorney, Agent, or Firm*—Chris P. Konkol

[57] ABSTRACT

The present invention discloses 1,3-dialkylimidazole-2-thiones catalysts for epoxy/anhydride reactions (and other reactions) and a method of making these catalysts. Epoxy/anhydride coatings containing these improved catalysts offer the following advantages: improved appearance (especially since even weeks after application the coatings still have a "wet" look); better pot-life; improved resistance to alkaline substances which will improve durability; improved solubility; and coatings which have a reduced volatile organic content (VOC).

3 Claims, No Drawings

1,3-DIALKYLIMIDAZOLE-2-THIONE CATALYSTS AND METHOD OF MAKING SAME

This is a continuation application under 37 CFR 1.60, of pending prior application Ser. No. 07/389,895, now abandoned, filed on Aug. 4, 1989

FIELD OF THE INVENTION

We have discovered that 1,3-dialkylimidazole-2-thione compounds are useful for catalyzing crosslinking reactions between polymers with pendent anhydrides and polymers with hydroxyl or epoxy functionality. A novel method of making the 1,3-dialkylimidazole-2-thione compounds is also disclosed. The use of 1,3-dialkylimidazole-2-thione catalysts is especially useful in the ambient cure of coatings containing a polymer having anhydride groups, and a polyepoxide or polyhydroxyl crosslinking agent. These novel catalysts form epoxy/anhydride resins useful in coatings with a number of significant advantages.

PRIOR ART

Coating compositions containing epoxy/anhydride resins are known in the art as shown by U.S. Pat. No. 4,816,500 assigned to Du Pont and commonly assigned patent application Ser. Nos. 07/212,298 U.S. Pat. No. 4,906,677; 07/212,053 U.S. Pat. No. 4,908,397; 07/212,054 now abandoned; 07/212,055 U.S. Pat. No. 5,017,435; 07/212,052 now abandoned and 07/253,991 now abandoned. These references generally disclose and claim coating compositions having a binder comprising (a) 50-95% by weight, based on the weight of the binder, of an acrylic polymer having at least two reactive anhydride groups, which consists of polymerized monomers of an ethylenically unsaturated anhydride and polymerized monomers selected from the group consisting of alkyl methacrylate, alkyl acrylate and any mixtures thereof, wherein the alkyl groups have 1-8 carbon atoms and the polymer has a weight average molecular weight of about 2,000-50,000; (b) 5-50% by weight, based on the weight of the binder, of a glycidyl component having at least two reactive glycidyl groups; (c) 0.1-5% by weight, based on the weight of the binder, of a catalyst (e.g. triethylene diamine, amine-borane adducts and phosphonium catalysts); and (d) assorted other additives which improve the properties of the coating. None of the disclosures show or suggest the use of 1,3-dialkylimidazole-2-thiones to catalyze the crosslinking reaction between the epoxy and the anhydride.

An unrelated reference found in *Organic Syntheses*, 1986, Vol 64, page 92 shows the preparation of 1,3-dimethylimidazole-2-thione. However this reference does not disclose other 1,3-dialkylimidazole-2-thiones, nor does it disclose or suggest the use of 1,3-dimethylimidazole-2-thione as a crosslinking catalyst.

SUMMARY OF THE INVENTION

The present invention describes the use of 1,3-dialkylimidazole-2-thiones as a catalyst for epoxy/anhydride reactions (and other reactions) and a method of making these catalysts. Epoxy/anhydride coatings containing these improved catalysts offer the following advantages: improved appearance (especially since even weeks after application the coatings still have a "wet" look); better pot-life; improved resistance to alkaline substances which will improve durability; improved solubility; and coatings which have a reduced volatile organic content (VOC).

The 1,3-dialkylimidazole-2-thiones of the present invention have the following structure:

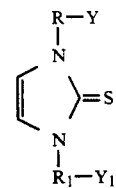

where R and $R_1$ are alkylene $C_1$ to $C_{14}$ (straight chain or branched) and Y and $Y_1$ are H, OH, $CO_2H$, aryl, ether, amine, perfluoroalkyl, amide, nitrile, or olefin. (Typically Y and $Y_1$ are H thus the nitrogens usually bear unsubstituted alkyl groups).

DETAILED DESCRIPTION OF THE INVENTION

The present invention describes the use of 1,3-dialkylimidazole-2-thiones as a catalyst for epoxy/anhydride resins which are used in paints, coatings, laiminates, moldings, castings and adhesives. These catalysts improve appearance (especially since even weeks after application the coatings still have a "wet" look); pot-life; resistance to alkaline substances which will improve durability; solubility; and VOC.

Typically, the reactive components used for making an epoxy/anhydride coating or hydroxyl/anhydride coating are an anhydride bearing polymer, copolymer or monomer and an epoxy or hydroxyl bearing polymer, copolymer or monomer. The anhydride, epoxy or hydroxyl bearing reactants may be in a solvent. These components along with a catalyst are often provided to the user in separate containers and are mixed on demand.

We have also found that 1,3-dialkylimidazole-2-thiones can be used to catalyze the crosslinking reaction between acid functional compounds and compounds with epoxy functionality. This is shown in Example 5 where an acid functional polymer is used in conjunction with an anhydride functional polymer and both are crosslinked with an epoxy functional compound.

The anhydride component of the epoxy/anhydride resins which are useful for the curing agents of this invention, may be any polymer or copolymer with a weight average molecular weight of less than 100,000 containing at least two reactive anhydride groups. Also low molecular weight monomeric anhydrides may be used.

Preferred anhydride components are copolymers prepared from one or more of the monomers of styrene, methacrylate, or acrylates with one or more of the monomers of itaconic acid, itaconic anhydrides, maleic anhydride or isobutenyl succinic anhydride. (After formation of the polymer the itaconic acid which is contained in the polymer is converted to the anhydride). As will be apparent to one skilled in the art there are a number of other monomers which could also be used to form the anhydride polymer. Some of these different monomers are disclosed in U.S. Pat. No. 4,816,500 which is incorporated herein by reference.

The epoxy component of the epoxy/anhydride coatings may be any polymer, copolymer or compound with a weight average molecular weight of less than 100,000 containing at least two epoxy groups. Also low molecular weight monomeric epoxies may be used. Preferred epoxy components are copolymers prepared from alkyl (meth)acrylates [hereinafter "(meth)acrylates" refers to either acrylates or methacrylates] with glycidyl (meth)acrylates. These prefered polymers may be used by themselves or in combination with the polyglycidylethers of sorbitol. Other preferred epoxies are Araldite CY-184 ® (from Ciba-Geigy Corporation) and epoxies based on Bisphenol A such as Epon 1001 ® (available from Shell Chemical Company). As will be apparent to one skilled in the art there are a number of different monomers which could also be used to form the epoxy polymer. Some of these different monomers are also disclosed in U.S. Pat. No. 4,816,500.

The hydroxyl containing compounds which can be used as a substitute or in addition to the epoxy containing compounds are polymers or copolymers containing hydroxy functionality with a weight average molecular weight of less than 100,000 containing at least two hydroxly groups. Low molecular weight monomeric hydroxyl compounds may also be used. Prefered hydroxyl compounds are copolymers containing alkyl (meth)acrylates and hydroxy functional (meth)acrylates. Also hydroxy functional polyesters can be used.

The acid functional compounds that may be used are monomeric, oligomeric, or polymeric which may or may not contain hydroxyl functionality. If polymeric, the compounds are typically formed by polymerizing monomers of alkyl (meth)acrylates where the alkyl groups have 1-12 carbon atoms and ethylenically unsaturated acids. Optionally, the acid functional polymer can also contain other components such as styrene, acrylonitrile, methacrylonitrile in amounts of about 0.1-50% by weight.

The coating composition formed using the components described above may contain 20% to 80% of the polymer or copolymer having at least two anhydride groups and 80% to 20% of the polymer or copolymer having at least two epoxy groups (or hydroxyl groups). The coating composition may also contain components such as monomeric anhydrides; acid functional monomeric, oligomeric or polymeric components which may or may not contain hydroxyl functionality (if there are acid functional groups present there must also be epoxy groups present in order to get cure); hydroxy functional polymers; and self-stabilized dispersed resins. Examples of monomeric anhydrides are methyl hexahydrophtalic anhydride and the like. Examples of such acid functional components are glycolic acid and acrylate/methacrylic acid copolymer and the like.

None of the components should contain any substituents which would interfere with the curing process.

As discussed above the catalyst for the epoxy/anhydride coating is 1,3-dialkylimidazole-2-thione. The catalyst is present at a level of 1-10% by weight, preferably about 4-6%, of the total binder. The 1,3-dialkylimidazole-2-thione is preferably made in two reation steps.

Although another method of making the 1,3-dialkylimidazole-2-thiones through a potassium carbonate route was disclosed in *Organic Syntheses*, 1986, Vol 64, page 92, this prior method provides yields of only about 60-70% compared with the current 2-step method which gives yields of as high as 90%. Furthermore, the two step method is simpler to operate than the previous potassium carbonate method. (A comparative example of the potassium carbonate method is shown in Example 2).

The first step in the two step process is reacting 1-alkylimidazole and alkyl halide (substituted or unsubstituted) to yield a N-alkyl-N'-alkylimidazolium halide.

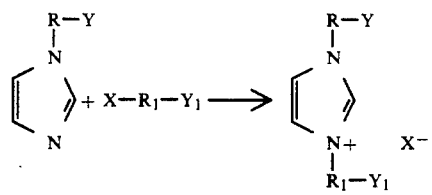

where X is halogen and R, $R_1$, Y, and $Y_1$ are defined as above

The 1-alkylimidazole and alkyl halide are preferably added in a 1:1 molar ratio. However, an excess of either may be used, but will result in a waste of starting material. The reaction may be done in the presence of an organic solvent, however, it is preferred that the reaction be done neat so that no seperation step is needed to isolate the N-alkyl-N'-alkylimidazolium halide. If a solvent is used, the solvent chosen should not react with the starting materials or product. Preferred solvents are toluene, methylene chloride, and methanol.

The reactants and solvents must be substantially dry. Most preferably they should contain less than 0.01% water, more preferably less than 0.1% water and preferably less than 0.5% water. The reaction temperature changes as the reactants change. If a heavy halide (i.e. iodide) is used then the reaction can proceed at room temperature. If a lighter halide is used then the reaction should be heated to between 40° C. to 120° C. (depending on the reactants). The time it takes for the reaction to go to completion also varies according to reactants from 2 to 48 hours.

In the second reaction step the product from the first reaction step, N-alkyl-N'-alkylimidazolium halide, is reacted with a suspension of sulfur and a base in a solvent to give the final catalyst 1,3-dialkylimidazole-2-thiones.

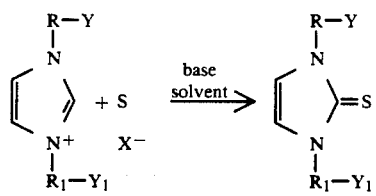

In this second reaction step, the preferred ratio of N-alkyl-N'-alkylimidazolium halide to sulfur to base is 1:1:1. Excesses of any of the three may be used but will result in a waste of starting material. The reactants and solvents must be substantially dry. Most preferably they should contain less than 0.01% water, more preferably less than 0.1% water and preferably less than 0.5% water. Preferably, the addition of the ingredients should be such that the base and N-alkyl-N'-alkylimidazolium halide are not in contact without sulfur. Usually the sulfur and base are premixed in solvent and then the N-alkyl-N'-alkylimidazolium halide is added to that mixture. The solvent is preferably a volatile alcohol. Most preferably the solvent is methanol. The base can be any alkali metal alkoxide. Preferably the base is sodium methoxide.

Preferably the reaction takes place at room temperature. However, it is possible for the reaction to take place anywhere from 20° to 80° C. and it normally takes between two to forty-eight hours. After the reaction has gone to completion, it is possible to separate the alkali metal halide from the 1,3-dialkylimidazole-2-thiones by either solvent evaporation, water extraction or filtration.

Our most preferred 1,3-dialkylimidazole-2-thione is 1-n-butyl-3-methylimidazole-2-thione. This compound is made as shown in Example 1. Other preferred 1,3-dialkylimidazole-2-thiones are 1-n-octyl-3-methylimidazole-2-thione (see Example 2), 1-n-propyl-3-methylimidazole-2-thione (see Example 3), and N,N'-diethylimidazole-2-thione.

Typical solvents used to prepare the anhydride acrylic polymer, and used as a diluent for the coating composition are as follows: toluene, xylene, butyl acetate, ethylbenzene, higher boiling aromatic hydrocarbons, amyl acetate, ethyl acetate, propyl acetate, ethylene or propylene glycol mono alkyl ether acetates and so forth.

In addition to the solvents listed above, certain alcoholic solvents are also useful. The alcoholic solvents under certain use conditions convert portions of the anhydride to a half ester also useful as reactants in this system. Examples of such alcohols are propanol, isobutanol, methanol, isopropanol, tertiary butanol, n-butanol, propylene glycol monomethyl ether, ethylene glycol monobutyl ether, and other alcoholic solvents.

Generally, the composition is applied by conventional techniques such as spraying and electrostatic spraying. The resulting coating can be dried and cured at ambient temperatures or can be cured at elevated temperatures of 60° to 200° C. The coating can be applied in pigmented or nonpigmented (clear) form. At ambient temperatures, the coating dries to a tack free condition in about 180 minutes and in about 24 hours the coating is substantially cured. In about 5-7 days, the coating is completely cured. Coatings are applied to form a finish about 0.5-5 mils thick, and preferably 1-2 mils thick. The finish has excellent gloss, retention of the "wet" look even weeks after application, good pot-life, good resistance to alkaline substances, good adhesion to substrate, good hardness and fast dry times.

To improve weatherability of the clear finish of the coating composition, about 0.1-5%, by weight, based on the weight of the binder, of an ultraviolet light stabilizer or a combination of ultraviolet light stabilizers can be added. These stabilizers include ultraviolet light absorbers, screeners, quenchers and specific hindered amine light stabilizers. Also, about 0.1-5% by weight, based on the weight of the binder, of an antioxidant can be added.

Typical ultraviolet light stabilizers that are useful are disclosed in U.S. Pat. No. 4,816,500.

Generally, when the coating composition of this invention is used as a clear coating, it is applied by conventional spraying techniques to a color or base coat of an automobile or truck. The coatings are baked at about 60° to 140° C. for about 10 to 40 minutes. In refinishing automobiles and trucks, the clear coating is applied to a color coat and then can be dried at ambient temperatures or baked to form a clear finish. The resulting clear coat or finish is about 1-5 mils thick, preferably 1-2 mils thick, and has excellent gloss, good adhesion to the color coat, good hardness, and good retention of the "wet" look even weeks after application.

The composition can be pigmented to form a colored finish or primer. About 0.1-200% by weight, based on the weight of the binder, of conventional pigments can be added using conventional techniques in which a mill base containing pigment, dispersant and solvent is first formed. The mill base is then mixed with the composition to form a colored composition. This composition can be applied and cured as shown above.

The following examples illustrate the invention. All parts and percentages, unless otherwise stated, are on a weight basis. The examples are merely illustrative and should not be read in any way to limit the scope of the invention.

EXAMPLE 1

Preparation of 1-n-Buty-Methylimidazole-2-Thione

A 3 liter single neck round bottom flask is equipped with a condenser and nitrogen bubbler. The flask is charged with 500 grams (6.1 mole) 1-methylimidazole and 650 grams (7.0 mole) n-butyl chloride. While stirring, the mixture is heated to reflux, 80° C. (pot temp). The mixture is refluxed for 16 hrs (the pot temperature is gradually increased to 110° C. over this time). The product is allowed to cool to room temperature and may crystallize on cooling.

The N-methyl-N'-n-butylimidazolium chloride, from the previous reaction, is dissolved into 500 ml anhydrous methanol. The methanol solution is cannulated into a 10 liter single neck flask containing a suspension of sulfur and sodium methoxide in anhydrous methanol (prepared by dissolving 140.3 grams (6.1 mol) sodium metal in 5.0 liter anhydrous methanol then adding 196 grams (6.1 mol) lac sulfur). The reaction is stirred for 24 hrs at 23° C. and then checked by $^1$H nuclear magnetic resonance (NMR) to assure completion. The reaction mixture is then pressure filtered through Celite ® to remove sodium chloride. The clear solution is acidified with 6N HCL to pH 5.0. A small amount of yellow solids precipitate out of the solution and are filtered off through Celite ®. The solution is concentrated on a rotary evaporator to leave a dark oil. The oil is vacuum distilled, 105° C./$10^{-2}$ torr, from KOH pellets to give a clear to slightly yellow colored oil. The yield is 886.1 grams (85.3%). The $^1$H NMR (CD$_3$CN) δ0.93 (t,3H,CH$_2$CH$_3$); 1.30 (tq,2H,CH$_2$CH$_3$); 1.63(tt,2H,NCH$_2$CH$_2$); 3.49(s,3H,NCH$_3$); 3.96(t,2H,NCH$_2$); 6.84(s,2H,NCH). Density-1.04 g/ml.

EXAMPLE 2

Preparation of 1-n-Octyl-3-Methylimidazole-2-Thione Using the Potassium Carbonate Method In the hood, a 0.5 liter round bottom flask equipped with a condenser and nitrogen bubbler, is charged with 65.70 grams (0.5 mol) 1-methylimidazole, 154.5 grams (0.8 mol) 1-bromooctane, and 100 ml acetonitrile. While stirring, the light yellow colored reaction mixture is heated to reflux, 97° C., and refluxed for about 1.5 hour. The mixture, now slightly darker in color, is then cooled to room temperature. The NMR is checked to assure completion and then the acetonitrile is removed under reduced pressure. This amber colored imidazolium bromide (220.0 grams, 0.8 mol) is placed in a 2 liter round bottom flask charged with 76.9 grams (2.4 mol) sulfur, and one 1 liter methanol. To this 221.38 grams (2.0 mol) of potassium carbonate is added in a single portion. A Drierite ® drying tube is attached to the flask and the reaction mixture is allowed to stir for 24 hours. The reaction mixture is checked by $^1$H NMR to assure completion. The bright yellow mixture is then filtered through a course fritted glass funnel. The filter cake is washed with methanol to extract any remaining product. The methanol is removed on a rotary evaporator. The dark red oil is then acidified with 1N HCl to pH 5.0 and filtered to remove excess sulfur. The solution is concentrated via rotary evaporator, then vacuum distilled from zinc powder to give 125 grams (a yield of 69%) of a dark red oil. The $^1$H NMR (CD$_3$)$_2$CO-7.00(m,NCH,2H); 4.02(t,NCH$_2$,2H), 3.52 (s,NCH$_2$,3H); 1.74(m,NCH$_2$C,H$_2$,2H); 1.31(m,(CH$_2$)$_5$,10H); 0.87(m,(CH$_2$)$_5$CH$_3$,3H).

EXAMPLE 3

Preparation of 1-n-Propyl-3-Methylimidazole-2-Thione

In the hood, a 200 ml single neck round bottom flask is equipped with a condenser and nitrogen bubbler. The flask is charged with 33.6 grams (0.41 mole) 1-methylimidazole and 55.5 grams (0.45 mol) 1-bromopropane. While stirring the mixture is heated to reflux, 70° C. (pot temperature). The mixture is refluxed for 16 hrs (the pot temperature is gradually increased to 110° C. over this time). The product is allowed to cool to room temperature. The $^1$H NMR is checked to assure completion. The NMR shows a single product with resonances in the expected regions.

The N-methyl-N'-n-propylimidazolium bromide from the previous reaction is dissolved in 50 ml anhydrous methanol. The methanol solution is cannulated into a 500 ml single neck flash containing a suspension of sulfur and sodium methoxide in 200 ml anhydrous methanol (prepared by dissolving 9.43 grams (0.41 mol) sodium metal in anhydrous methanol then adding 13.15 grams (0.41 mol) lac sulfur). The reaction is stirred for 24 hrs at 23° C. and then checked by $^1$H NMR to assure completion. The reaction mixture is then pressure filtered through Celite ® to remove sodium chloride. The clear brown solution is acidified with 1 N HCl to pH 5.0. The solution is concentrated via rotary evaporator to give a dark brown oil. The oil is then vacuum distilled (85°-100° C./0.1 mm Hg) from KOH to give 51.82 grams (a yield of 81%) of colorless oil. $^1$H NMR (CD$_2$Cl$_2$)δ0.93 ppm (t,CH$_2$CH$_3$,3H); 1.77(dq,CH$_2$CH$_3$,2H); 3.55(s,NCH$_3$,3H; 3.95(t,NCH$_2$,2H); 6.71(s,NCH,2H).

EXAMPLE 4

Preparation of an Ambient Cure Coating Using a Thione Catalyst

Preparation of a Polyanhydride

| Part | Ingredient | Parts by Weight |
|---|---|---|
| 1 | Xylene | 232.10 |
| 2 | Styrene | 91.70 |
|   | Butylmethacrylate | 122.20 |
|   | Butylacrylate | 232.2 |
|   | Xylene | 50.20 |
| 3 | Itaconic acid | 191.60 |
|   | Xylene | 60.00 |
| 4 | 75% Tert-Butylperoxyacetate Initiator ("Lucidol 70" from the Lucidol Division of Penwalt Corporation) | 30.50 |
|   | Propyleneglycolmonomethyletheracetate | 12.10 |
|   | Xylene | 57.50 |
| 5 | Propyleneglycolmonomethyletheracetate | 102.10 |
| 6 | Propyleneglycolmonomethyletheracetate | 102.10 |

Part 1 was added to a reactor equipped with a thermometer, stirrer, dropping funnel, water separater, nitrogen purge and condenser and heated to reflux. Parts 2 and 3 were premixed and added to the reactor over 3 hours simultaneously. Part 4 was premixed and added to the reactor over 3 hours and 20 minutes beginning with the start of Parts 2 and 3. The batch was then maintained at reflux until 25.2 parts of water were collected in the water separater. Part 5 was then added to the batch and 341.3 parts of solvent were removed by distillation. Part 6 was then added to the batch and the batch was cooled.

This polymer solution had a Garner-Holdt viscosity of Z1+½ and a measured solids of 69.7%. The anhydride content was determined to be 0.91 Meq/gm and the acid content to be 0.19 Meq/gm. The molecular weight was measured by gel permeation chromatography to be Mn=2074 and Mw=5093.

Preparation of a Polyol

| Part | Ingredient | Parts by Weight |
|---|---|---|
| 1 | Methyl N-amyl ketone | 170.85 |
| 2 | Methyl N-amyl ketone | 61.90 |
|   | 75% t-Butylperacetate Initiator ("Lupersol 70" from the Lucidol Division of Pennwalt Corporation) | 27.74 |
| 3 | Styrene | 143.88 |
|   | Ethylmethacrylate | 143.88 |
|   | Laurylmethacrylate | 115.12 |
|   | Hydroxyethylacrylate | 172.63 |
|   | Total | 836.00 |

Part 1 was added to a reactor equipped with a stirrer, thermometer, condenser, nitrogen purge and feed funnel and heated to reflux. Part 2 was premixed and added to the reactor over 165 minutes. Part 3 was premixed and added to the reactor over 150 minutes beginning with the start of Part 2. The batch was then held at reflux for 2 additional hours and then cooled. The resulting polymer had a weight percent solids of 70% and a hydroxyequivalent weight on solids was 386.7 gms per equivalent.

Preparation of a Polyepoxide

| Part | Ingredient | Weight |
|---|---|---|
| 1 | Butylacetate | 244.67 |
|   | Toluene | 25.51 |
|   | Ethylacetate | 41.39 |
| 2 | Glycidylmethacrylate | 233.12 |
|   | Butylacetate | 62.29 |
|   | Butylmethacrylate | 155.41 |
|   | "Vazo 67" Initiator (from DuPont) | 18.68 |
| 3 | Butylacetate | 14.32 |
|   | Propyleneglycolmonomethyletheracetate | 48.32 |
|   | "Vazo 67" Initiator (from DuPont) | 4.77 |
|   | Total | 848.48 |

Part 1 was added to a reactor equipped with a stirrer, thermometer, condenser, nitrogen purge, and feed funnel and heated to reflux. Part 2 was premixed and added to the reactor over 2 hours maintaining reflux. Part 3 was premixed and added over 30 minutes after part 2 was finished. The batch was held at reflux for 30 more minutes then cooled and filled out. The resulting polymer's weight percent solids was 45.7% and the epoxyequivalent weight on solids was 236.7 gms per equivalent.

Preparation of Coatings Using Various Catalysts

Coating compositions were prepared by thoroughly blending the following components. As can be seen from the table below, six different coating compositions were prepared using the polymers described above, other additives and a catalyst or mixture of catalysts. Coatings A and E contained only "thione" catalyst, while coatings B, C and D contained a mixture of "thione" and amine catalyst. Coating U contained only amine catalyst.

| Components (Code) | A | B | C | D | E | U |
|---|---|---|---|---|---|---|
| Polyol (from above) | 13.5 | 13.5 | 13.5 | 13.5 | 13.5 | 13.5 |
| 10% TEDA | 0 | 3.157 | 0 | 0 | 0 | 6.30 |
| 30% MTEDA | 0 | 0 | 1.184 | 0 | 0 | 0 |
| 30% MTEDA:BH3 | 0 | 0 | 0 | 1.315 | 0 | 0 |
| 30% BTI | 3.195 | 3.195 | 3.195 | 3.195 | 6.372 | 0 |
| 30% Tin328 | 2.1 | 2.1 | 2.1 | 2.1 | 2.1 | 2.1 |
| 10% Tin144 | 6.3 | 6.3 | 6.3 | 6.3 | 6.3 | 6.3 |
| Pgmmether | 4.121 | 4.159 | 4.164 | 4.169 | 4.237 | 4.08 |
| Solv Mix* | 12.02 | 9.526 | 11.582 | 11.533 | 10.845 | 8.23 |
| Polyanhydride (from above) | 20.763 | 20.763 | 20.763 | 20.763 | 20.763 | 20.76 |
| Polyepoxide (from above) | 9.779 | 9.779 | 9.779 | 9.779 | 9.779 | 9.78 |
| "Denecol Ex622" (from Nagase America Corp.) | 3.15 | 3.15 | 3.15 | 3.15 | 3.15 | 3.15 |

Code Description
30% BTI 1-n-butyl-3-methylimidazole-2-thione 30% solution in xylene
10% TEDA Triethylenediamine 10% solution in xylene
30% MTEDA:BH3 Borane adduct of MethylTEDA 30% in acetone
10% TIN144 "Tinuvin 144" light stabilizer from Ciba-Geigy 10% solution in xylene
30% TIN328 "Tinuvin 328" U.V. absorber from Ciba-Geigy 30% solution in xylene
PGMMETHER Propyleneglycolmonomethylether
30% MTEDA Methyltriethylenediamine 30% solution in xylene
*The solvent mix used was:

| | |
|---|---|
| Butylacetate | 19.80 |
| Propyleneglycolmonomethyletheracetate | 13.2 |
| Xylene | 23.1 |
| N-Hexylacetate | 43.9 |

Films of the above compositions were cast using a 0.010 inch draw down blade onto panels made of glass and thermoplastic polyolefin. Descriptions of the tests performed on the coatings are described at the end of this Example.

Test Results After One Day Cure at 25° C.

| Coating | Geltime (hours) | Persoz Hardness 1 Day | Dry Film Thickness Microns |
|---|---|---|---|
| A | 9.00 | 90 | 75 |
| B | 3.25 | 129 | 65 |
| C | 4.33 | 114 | 75 |
| D | 8.08 | 115 | 65 |
| E | 5.08 | 154 | 65 |
| U | 1.67 | 117 | 65 |

Test Results After Seven Days Cure at 25° C.

| Coating | Persoz Hardness | Swell Ratio in $CH_2Cl_2$ | 5% Naoh | 10% Sulf | Ford #24 |
|---|---|---|---|---|---|
| A | 178 | 1.64 | 3 | 5 | 4 |
| B | 193 | 1.58 | 3 | 5 | 4 |
| C | 183 | 1.6 | 3 | 5 | 4 |
| D | 207 | 1.61 | 4 | 5 | 4 |
| E | 200 | 1.54 | 4 | 4 | 4 |
| U | 168 | 1.67 | 3 | 5 | 4 |

Description of various tests in Example 4 Gel Time $T_0$ = The clock time when all the ingredients are mixed to form a complete solution of reactive binders and catalyst.

$T_1$ = The clock time when this mixture forms a tail on the bubble in a Gardner-Holdt tube.

Gel time = $T_1 - T_0$.

Persoz Hardness

The solution of mixed ingredients is drawn down on a 4" by 12" glass. The solids are normally 45% or 50% in our experiments. We use a 0.010" doctor blade. Film thickness will be in the range 45 to 60 microns. In 24 hrs (±2 hrs) the hardness of the film is measured by the Byk Mallinkrodt Pendulum Hardness Tester with a Persoz Pendulum.

Swelling Ratio

The solution of mixed ingredients is drawn down on a panel of TPO (Thermoplastic Polyolefin). On test day a free film is lifted off the TPO with a single edge razor. A circular specimen is punched from the film with a 3.1 mm grid punch. We usually sandwich the film in between aluminum foil for punching so that the specimen has enough weight to fall down the barrell of the punch into the catch pan. The 3.1 mm specimen is then mounted on a slide and its diameter measured in filar units using a microscope equipped with a filar micrometer. This diameter is $D_0$. Methylene chloride is dropped onto the specimen; swelling starts; a cover glass is put over the swelling specimen; swelling reaches its equilibrium value. The swollen diameter is $D_s$.

The swelling ratio is calculated as follows:

$$\text{Swell Ratio} = \frac{(D_s/2)^2}{(D_0/2)^2}$$

This is the ratio of the swollen area to the unswollen area.

Swelling Ratio Comments

We have used swelling ratio as measure of cure in hundreds of screening tests and have adopted the following guideline for describing cure . . .

| Cure | Swelling Ratio $CH_2CL_2$ 7-8 Days |
|---|---|
| Excellent | <1.55 |
| Very Good | 1.55-1.65 |
| Good | 1.65-1.75 |
| Fair | 1.75-1.85 |
| Poor | 1.85-2.00 |
| Very Poor | >2.00 |

Chemical Spot

The film drawn down on glass is exposed to drops of various chemicals such as 5% NAOH and 10% H2SO4. After one hour the spot is wiped away and the exposed coating is checked for softening, swelling, discoloration and wrinkling. Using 5 as a perfect rating a point is deducted for each of the aforementioned defects found. For example a coating that turns yellow and softens loses 2 points and gets a rating of 5−2=3.

Summary of Results

As can be seen from the above results, Coating E with "thione" catalyst at the same level as the coating with only amine catalyst (Coating U) has longer gel time, better one day hardness, better seven day hardness and better cure (as indicated by a lower swelling ratio) than the amine based system. (Coating E and Coating U both have catalyst levels of 0.0357 equivalents per hundred grams of total binder).

Even Coating A with only half the level of "thione" catalyst has only slightly less hardness after one day's cure and comparable hardness and cure after seven days when compared to Coating U. Significantly, the gel time, indicative of useful pot life, is much longer for Coating A than Coating U.

Coating B,C and D, which are blends of the "thione" catalyst with various amine catalysts show the possibility for getting better balances of pot-life and cure by mixing the thione catalyst and amine catalyst.

EXAMPLE 5

Coating Composition that Requires Baking to Cure

Preparation of Acid Polymer Component

A butyl acrylate-methacrylic acid copolymer was prepared as follows:

A reactor was charged with the following:

| | |
|---|---|
| Propyleneglycolmonomethylether-acetate (PM acetate) | 1604.0 parts |
| Butyl acetate | 441.0 parts |
| Xylene | 1243.0 parts |

This mixture was heated with agitation under nitrogen to reflux. Then the following mixture was added at a uniform, linear rate over three hours while maintaining reflux.

| | |
|---|---|
| Butyl acrylate monomer | 2427.0 parts |
| Methacrylic acid monomer | 1630.0 parts |
| Tertiary butyl peroxyacetate ("Lucidol 70" from Pennwalt) | 224.0 parts |

Then the following mixture was added over ten minutes while maintaining reflux temperature:

| | |
|---|---|
| Xylene | 200.0 parts |
| Tertiary butyl peroxyacetate | 19.0 parts |

The mixture was maintained for one hour at reflux temperature and then diluted with the following:

| | |
|---|---|
| PM Acetate | 692.0 parts |
| Total | 8480.0 parts |

This polymer had a Garner-Holdt viscosity of Z1+½ and a measured solids of 52.3%. The acid content was determined to be 2.28 Meg/gm and molecular weight by gel permeation chromatography was Mn=2762, Mw=6108.

A coating composition using 1-n-butyl-3-methylimidazole-2-thione catalyst was prepared by thoroughly blending the following constituents:

| | Parts by Weight |
|---|---|
| Polyanhydride (from Example 4) | 453.2 |
| PM acetate | 38.2 |
| Methyl hexahydrophthalic anhydride | 57.5 |
| Resiflow S ® (acrylic flow additive from Estron Chemical Co.) | 3.4 |
| Butyl acetate | 118.7 |
| Araldite CY-184 ® (Epoxy resin from Ciba-Geigy) | 238.1 |
| Acid polymer (as prepared above) | 174.3 |
| Butanol | 38.8 |
| Tinuvin 292 ® (Ciba-Geigy hindered amine light stabilizer) | 13.2 |
| Tinuvin 1130 (Ciba-Geigy UV screener) | 20.1 |
| 25% 1-n-butyl-3-methylimidazole-2-thione in Butyl Acetate | 66.9 |
| Total | 1204.4 |

The resulting coating composition was reduced to a spray viscosity of 35 seconds measured with a No. 2 Zahn cup accomplished by adding butyl acetate.

The coating composition was sprayed onto a primed metal panel coated with a waterborne basecoat and cured at 180°-200° F. and provided a clear coat with excellent color, durability, humidity resistance, chemical resistance, and other film properties. The coating composition was also sprayed over solvent borne melamine cured basecoat and cured at 240°-284° F. The resulting coating exhibited excellent color, durability, humidity resistance, chemical resistance, and other film properties.

EXAMPLE 6

PIGMENTED COATING WITH THIONE CATALYST

Preparation of Hydroxy Functional Polymer "B"

| Part | Ingredient | Weight |
|---|---|---|
| 1 | Methyl n-amyl ketone | 339.830 |
| 2 | Methylmethacrylate | 94.970 |
|   | Styrene | 94.970 |
|   | Butylacrylate | 253.230 |
|   | Hydroxyethylacrylate | 189.940 |
|   | Methyl n-amyl ketone | 16.728 |
| 3 | Methyl n-amyl ketone | 47.345 |
|   | 75% t-butylperacetate Initiator ("Lupersol 70" from Pennwalt Corporation) | 21.080 |
| 4 | Methyl N-Amyl Ketone | −233.240 |
| 5 | Methyl N-Amyl Ketone | 40.147 |
|   | Yield | 865.000 |

Part 1 was added to a reactor equipped with a stirrer, thermometer, condenser, nitrogen purge and feed funnel and heated to reflux. Part 2 was premixed and added to the reactor over 225 minutes.

Part 3 was premixed and added to the reactor over 240 minutes beginning with the start of part 2. The batch was then held at reflux. For 1 additional hour, part 4 was then removed by distillation, the batch was cooled and pumped from the reactor. Part 5 was used to rinse the reactor and lines. The weight percent solids was 75% and the hydroxyequivalent weight on solids were 386.9 gms per equivalent.

Preparation of Polyepoxide Polymer "C"

| Part | Ingredient | Weight |
|---|---|---|
| 1 | Xylene | 137.408 |
| 2 | Glycidyl Methacrylate | 209.080 |
|   | Butylacrylate | 179.170 |
|   | Methyl Methacrylate | 209.080 |
|   | Xylene | 14.256 |
| 3 | Xylene | 40.992 |
|   | 75% T-Butylperacetate Initiator ("Lupersol 70" from Pennwalt Corporation) | 33.160 |
| 4 | Xylene | 18.951 |
| 5 | Xylene | 37.903 |
|   | Total | 880.000 |

Part 1 was added to a reactor equipped with a stirrer, thermometer, condenser, nitrogen purge, and feed funnel and heated to reflux. Part 2 was premixed and added to the reactor over 5 hours while maintaining reflux. Part 3 was premixed and added over 5 hours simultaneously with part 2. The batch was held at reflux for 45 more minutes then pumped to a prefilter tank. Part 4 is then added to the reactor, stirred to rinse the vessel, and pumped to the prefilter tank. Following filtration, part 5 is used for viscosity/solids adjustment. The weight percent solids was 70.0%.

Preparation of a White Dispersion

A white dispersion was prepared by mixing the following constituents into a blend tank:

| Part | Ingredient | Parts by Weight |
|---|---|---|
| 1 | Hydroxy functional Polymer "B" (prepared above) | 7.500 |
|   | Methyl n-amyl ketone | 16.670 |
| 2 | Titanium dioxide white pigment | 69.990 |
| 3 | Hydroxy functional Polymer "B" (prepared above) | 5.840 |
|   | Total | 100.000 |

Part 1 was added to the blend tank and mixed for 15 minutes. Part 2 was then added to the blend tank while mixing and then mixed for 30 minutes. Part 3 was then added to the blend tank while mixing and mixed for an additional 10 minutes. The resulting blend was put through a sand mill for fineness.

Preparation of Rheology Control Dispersion

A rheology control dispersion was prepared by mixing the following constituents into a blend tank:

| Part | Ingredient | Parts by Weight |
|---|---|---|
| 1 | Mixed methyl esters of succinic, glutaric and adipic acids (Dibasic Ester-DBE from E. I. duPont deNemours) | 7.500 |
|   | Ethyleneglycolmonobutyletheracetate | 20.240 |
|   | Denecol EX622 ® (Epoxy Resin from Nagase) | 65.800 |
| 2 | Colloidal Silica | 7.210 |
|   | Total | 100.000 |

Part 1 was added to the blend tank and mixed for 15 minutes. Part 2 was then added to the blend tank slowly while mixing and then mixed for an additional 10 minutes. The resulting blend was put through a sand mill for fineness.

Formulation of a White Enamel

| Part | Ingredient | Parts by Weight |
|---|---|---|
| 1 | White Dispersion (described above) | 818.280 |
|   | Denecol EX622 ® (Epoxy Resin from Nagase) | 106.380 |
|   | Araldite CY184 ® (Epoxy Resin from Ciba-Geigy) | 121.000 |
|   | Polyepoxide Polymer "C" (prepared above) | 87.020 |
|   | Silicone SF-69 ® (from General Electric) | 0.092 |
|   | Xylene | 4.508 |
|   | Rheology control dispersion (described above) | 171.170 |
|   | Various color dispersions (for controlling final color made like the white dispersion described above) | 2.550 |
|   | Total | 1311.000 |

Add all of the Part 1 ingredients in order while mixing. Mix dispersions before use. The ingredients are then mixed for 1 hour.

Preparation of an Activator Mixture

| Part | Ingredient | Parts by Weight |
|---|---|---|
| 1 | Polyanhydride Polymer (from Example 4) | 832.750 |
|   | Methylethylketone | 51.250 |
|   | Total | 884.000 |

The two ingredients from Part 1 were added in order while mixing. The mixture was mixed for 1 hour.

Coating compositions were prepared by thoroughly blending the following ingredients:

| Code | 1 | 2 | 3 | 4 | 5 | 6 |
|---|---|---|---|---|---|---|
| White Enamel Formulation | 131.1 | 131.1 | 131.1 | 131.1 | 131.1 | 131.1 |
| Activator Mixture | 88.4 | 88.4 | 88.4 | 88.4 | 88.4 | 88.4 |
| Ethanol | 18.5 | 18.5 | 18.5 | 18.5 | 18.5 | 18.5 |
| n-Butanol | 1.9 | 1.9 | 1.9 | 1.9 | 1.9 | 1.9 |
| Diethyleneglycolmonobutylether | 12.2 | 12.2 | 12.2 | 12.2 | 12.2 | 12.2 |
| Dimethylethanolamine | 1.5 | 1.5 | 1.5 | 1.5 | 1.5 | 1.5 |
| Tinuvin 292 R (Ciba Geigy) | 0.5 | 0.5 | 0.5 | 0.5 | 0.5 | 0.5 |
| Tinuvin 328 R (Ciba Geigy) | 0.5 | 0.5 | 0.5 | 0.5 | 0.5 | 0.5 |
| 10% TEDA (Air Products & Chemicals) | 1.5 | 0 | 0.7 | 0 | 0 | 0 |
| 30% MTEDA (Air Products & Chemicals) | 0 | 1.7 | 0 | 0.8 | 0.8 | 0 |
| 30% TEDA:BH3 | 0 | 0 | 0.8 | 0.8 | 0 | 0 |
| 30% BTI | 0 | 0 | 0 | 0 | 2.3 | 7.4 |

Films of the above compositions were spray applied to treated aluminum panels. A dry film thickness of approximately 2 mils and allowed to air dry for at least 2 weeks prior to testing chemical resistance. The tests performed on the coatings are described following the test results.

| TEST RESULTS | | | | | | |
|---|---|---|---|---|---|---|
| Chemical Spot Test Chemical | 1 | 2 | 3 | 4 | 5 | 6 |
| H3PO4-1% | NE | VSlSw | NE | NE | NE | NE |
| -10% | VSlSw | VSlSw | NE | InSw | InSw | NE |
| HNO3-1% | NE | NE | NE | NE | NE | NE |
| -10% | Mod-Sev Blst | Mod-Sev Blst | Sev Blst | Mod-Sev Blst | Sev Blst | Sev Blst |
| Morpholine-1% | NE | NE | NE | NE | NE | NE |
| -10% | NE | NE | InSw | InSw | InSw | NE |
| H2SO4-1% | InSw | NE | NE | InSw | NE | NE |
| -10% | InSw | InSw | InSw | InSw | InSw | NE |
| NaOH-1% | NE | NE | NE | NE | NE | NE |
| -5% | FR | FR | FR | FR | FR | NE |
| -10% | FR | FR | FR | FR | FR | FR |
| NH4OH-10% | NE | NE | NE | NE | NE | NE |

Rating Code
NE-No Effect
IN-Insignificant
VSl-Very Slight
Sl-Slight
Mod-Moderate
Sev-Severe
Blst-Blistering
FR-Film Removed
Sw-Swelling Description of Chemical Spot Test in Example 6

The cured film on the aluminum panel is exposed to drops of various chemicals such as 5% NAOH and 10% H2SO4 under individual watch glasses. After overnight exposure (18 hours) the spot is washed away and the exposed coating is checked for softening, swelling, discoloration, wrinkling, or complete removal. The condition of the spots that had undergone testing is then verbally described as above.

I claim:

1. A method of reacting, in the presence of a catalyst, compounds with anhydride or acid functionality with compounds with epoxy functionality, to form an epoxy-/anhydride coating, the improvement comprising employing a catalytically effective amount of a 1,3-dyalkylimidazole-2-thione within the following structural formula:

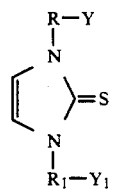

where R and $R_1$ are alkylene $C_1$ to $C_{14}$, straight chain or branched, and Y and $Y_1$ are H, OH, $CO_2H$, aryl, ether, amine perfluoroalkyl, amide, nitrile, or olefin.

2. The method of claim 1, wherein Y and $Y_1$ are hydrogen.

3. The method of claim 1, wherein said 1.3-dialkylimidazole-2-thione is selected from the group consisting of 1-n-octyl-3-methylimidazole-2-thione, 1-n-butyl-3-octyl-3-imidazole-2-thione, 1-n-propyl-3-methylimidazole-2-thione, N,N'-diethylimidazole-2-thione.

* * * * *